United States Patent [19]

Tachibana et al.

[11] Patent Number: 5,720,710
[45] Date of Patent: Feb. 24, 1998

[54] REMEDIAL ULTRASONIC WAVE GENERATING APPARATUS

[75] Inventors: Katsuro Tachibana; Shunro Tachibana, both of Fukuoka, Japan

[73] Assignee: Ekos Corporation, Bothell, Wash.

[21] Appl. No.: 272,538

[22] Filed: Jul. 11, 1994

[30] Foreign Application Priority Data

Jul. 12, 1993 [JP] Japan .................. 5-171687

[51] Int. Cl.$^6$ .................................................. A61N 7/00
[52] U.S. Cl. .................................................. 601/2; 604/20
[58] Field of Search .................. 601/2; 128/660.03; 604/20, 22; 310/316, 317

[56] References Cited

U.S. PATENT DOCUMENTS

| | | |
|---|---|---|
| 3,872,472 | 3/1975 | Moschgat .................. 340/384 |
| 3,893,106 | 7/1975 | Schulein .................. 340/384 |
| 4,052,977 | 10/1977 | Kay .................. 601/2 |
| 4,484,315 | 11/1984 | Hall .................. 367/139 |
| 4,821,740 | 4/1989 | Tachibana . | 
| 4,933,918 | 6/1990 | Landsrath et al. .................. 367/139 |
| 4,953,565 | 9/1990 | Tachibana . |
| 5,007,438 | 4/1991 | Tachibana . |
| 5,115,805 | 5/1992 | Bommannan et al. .................. 601/2 |
| 5,185,071 | 2/1993 | Umemura et al. .................. 128/660.03 |
| 5,267,985 | 12/1993 | Shimada et al. .................. 601/2 |

FOREIGN PATENT DOCUMENTS 3-63913  10/1991  Japan .

*Primary Examiner*—Brian L. Casler
*Attorney, Agent, or Firm*—Wilson Sonsini Goodrich & Rosati

[57] ABSTRACT

A remedial ultrasonic wave generating apparatus which allows highly efficient dispensation of a medicine without complicated preparations is provided. An ultrasonic wave generating apparatus for supplying an ultrasonic wave signal to a remedial ultrasonic oscillation element comprising an ultrasonic wave signal generating for generating an ultrasonic wave signal whose frequency randomly changes. The ultrasonic wave signal generating is constituted by, for example, a plurality of oscillation circuits oscillating at different frequencies and a switching circuit for randomly selecting one of the outputs of these oscillation circuits based on the output of a random number generating circuit.

15 Claims, 3 Drawing Sheets

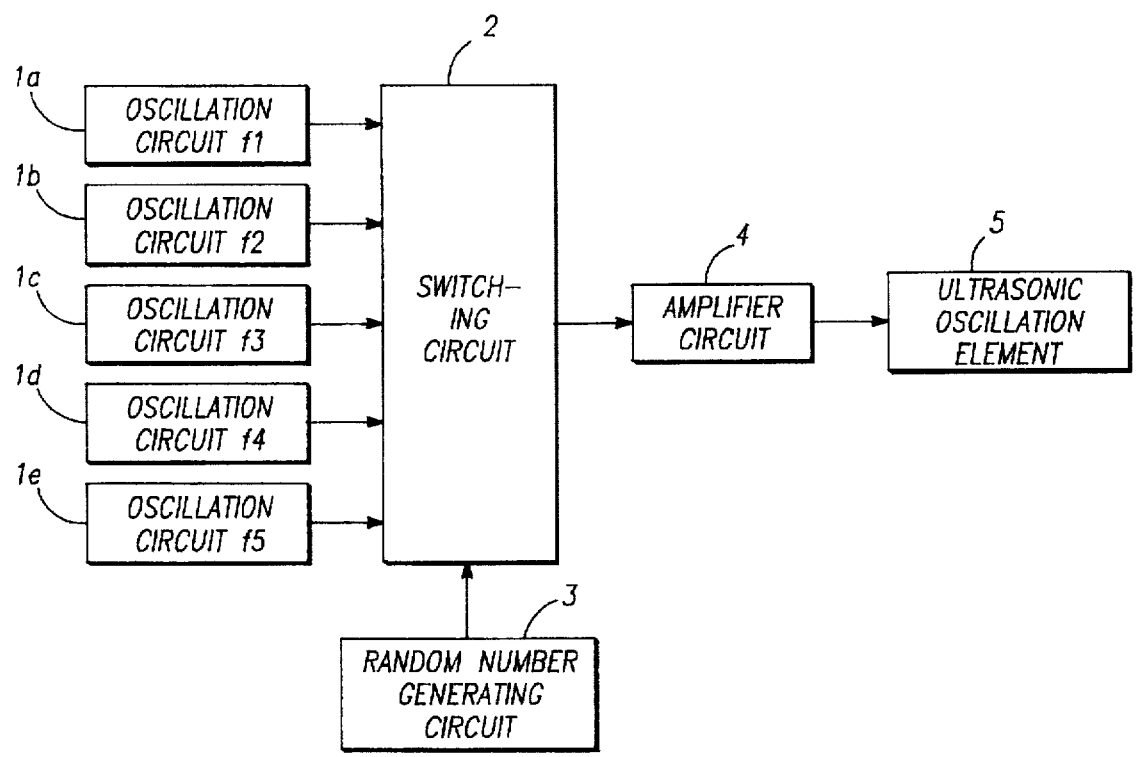
FIG.—1
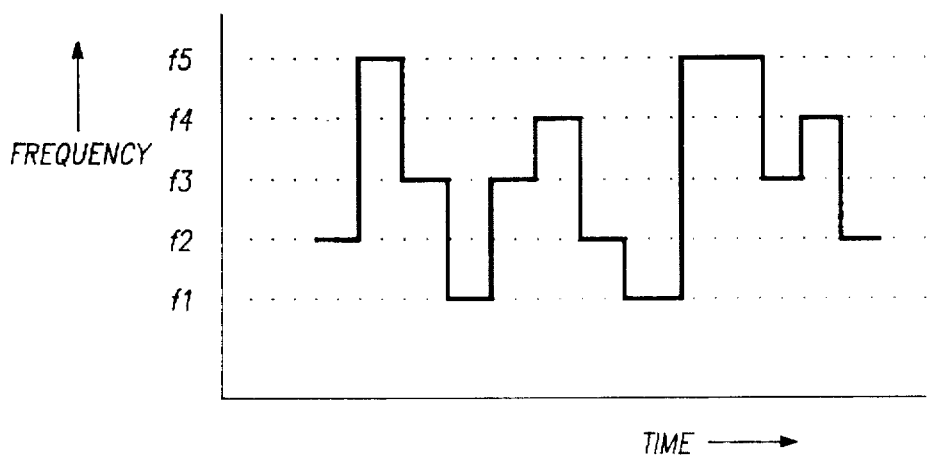
FIG.—2

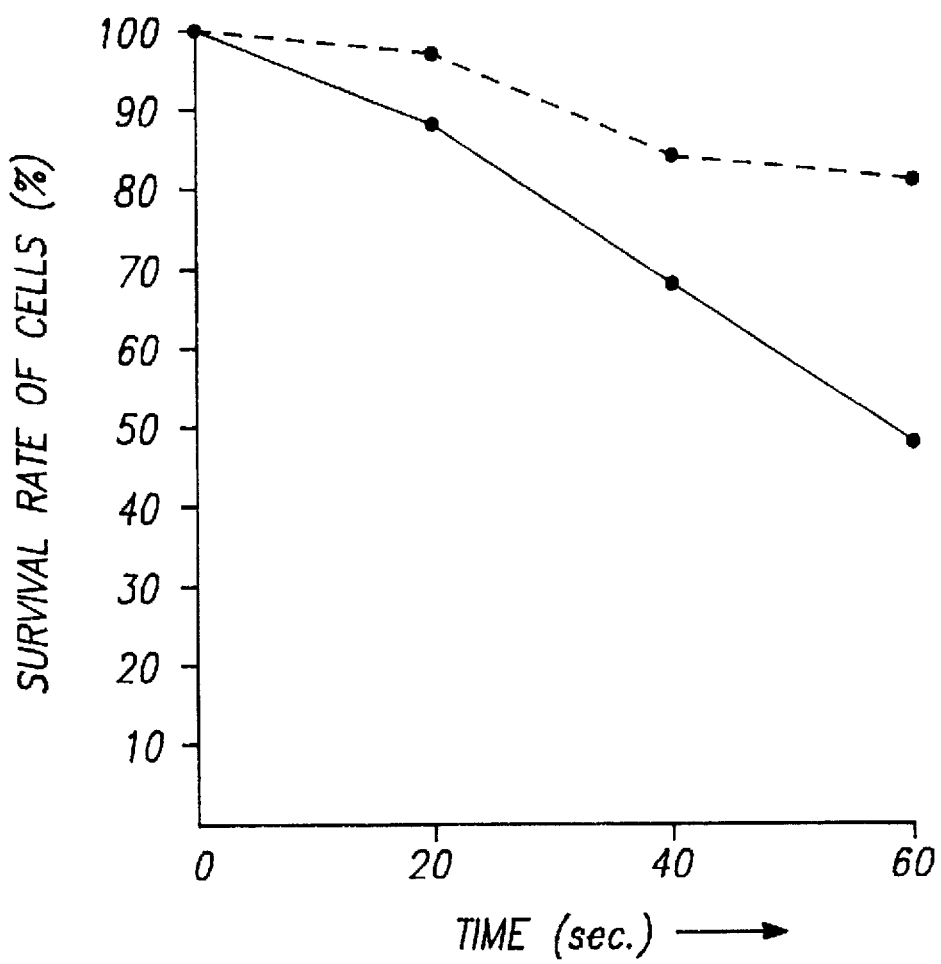
FIG.—6

5,720,710

REMEDIAL ULTRASONIC WAVE GENERATING APPARATUS

BACKGROUND OF THE INVENTION

1. Field of the Invention

The present invention relates to an apparatus for generating ultrasonic waves for improving the dispensation and effect of a medicine or a remedy.

2. Description of the Related Art

To improve the dispensation and effect of a medicine, application of ultrasonic waves has been conventionally carried out in the vicinity of the diseased part to which the medicine is dispensed.

For example, Japanese Patent Publication No. H3-36913 which corresponds to U.S. Pat. Nos. 4,821,740, 4,953,565 and 5,007,438 discloses an endermic dispensing tool having a medicine layer and an ultrasonic oscillation element contained in a common container wherein the medicine layer is disposed so that it is exposed directly or through a medicine-permeable member to the outside at a part of the container and the ultrasonic oscillation element is disposed so that it is acoustically coupled to the medicine layer.

In the endermic dispensing tool disclosed in the publication, an ultrasonic wave signal is supplied from an externally provided ultrasonic oscillator to the ultrasonic oscillation element which in turn causes ultrasonic oscillation at a predetermined frequency.

The ultrasonic oscillation element is attached to the forward end of a catheter which is inserted into the human body. Decomposition of a thrombus is encouraged by injecting thrombus decomposing medicine through the catheter with the ultrasonic wave applied to said thrombus.

The effect of a remedy can be improved by the use of ultrasonic waves during dispensation of a medicine as described above. The degree of the effect depends on various conditions, for example, the method of applying the ultrasonic wave, the frequency and strength of the ultrasonic wave, the density of the medicine, etc. Therefore, when an ultrasonic wave and medicine are used in tandem in a remedy, it is essential to provide conditions which will enable the greatest efficacy.

Although it is known that the efficacy of a remedy depends on the frequency of the ultrasonic wave which is used, the optimum frequency has not yet been identified. The reason is that there are factors with complicated correlations such as differences between objects to be treated, e.g., organic structures such as cells and thrombi, factors associated with the drugs (type, density, amount, etc.) and factors associated with the oscillation elements (shape, position, etc.).

Therefore, to actually dispense a medicine, for example, several ultrasonic wave generating apparatuses having different oscillation frequencies are prepared. The effect of the dispensation is first examined by driving the ultrasonic oscillation element at several different frequencies to obtain a frequency which seems to be the optimum. Then, the ultrasonic oscillation element is driven at this frequency to improve the dispensation of the medicine.

However, since the condition for dispensation changes each time a drug is delivered, the operation to find the optimum frequency must be repeated each time, which necessitates enormous time and labor.

For example, in remedies for thrombi using ultrasonic waves and thrombus decomposing medicine, the thrombi in the diseased parts do not always have the same structure. The stiffness, density and composition of a thrombus vary from person to person and depending on bloodstream, the density of red blood cells and the like. As a result, even if a particular sensitivity is exhibited at a particular frequency, it will be impossible to find that frequency in a short time. This has precluded this method from being effectively employed as an urgent remedy for cardiac infarctions or the like.

Further, in finding the optimum frequency, the effect of dispensation of the medicine is not examined at all frequencies but only at discrete frequencies. This can lead to a frequency being erroneously regarded as the true optimum frequency, making it impossible to obtain the maximum effect which would otherwise be available.

Under these circumferences, it is an object of the present invention to provide a remedial ultrasonic wave generating apparatus which allows highly efficient dispensation of a medicine without complicated preparatory operations.

SUMMARY OF THE INVENTION

According to the present invention, there is provided a remedial ultrasonic wave generating apparatus for supplying an ultrasonic wave signal to a remedial ultrasonic oscillation element, comprising an ultrasonic wave signal generating means for generating an ultrasonic wave signal whose frequency randomly changes.

According to the present invention, since the frequency of the ultrasonic waves supplied to the remedial ultrasonic oscillation element randomly changes, the ultrasonic oscillation includes frequency components in a very wide band when observed over time. Therefore, even if there are a variety of conditions for dispensation of a medicine, a frequency component which provides the maximum effect under each condition will be included in those frequency components. This makes it possible to dispense a medicine with high efficiency regardless of differences in conditions under which the medicine is dispensed.

BRIEF DESCRIPTION OF THE DRAWINGS

FIG. 1 is a block diagram showing a first embodiment of a remedial ultrasonic wave generating apparatus according to the present invention.

FIG. 2 is a graph showing random changes in an ultrasonic frequency.

FIG. 6 is a graph showing the difference in effect between a case wherein a frequency is changed in order and a case wherein the frequency is randomly changed.

DETAILED DESCRIPTION OF PREFERRED EMBODIMENTS

Figure 3:
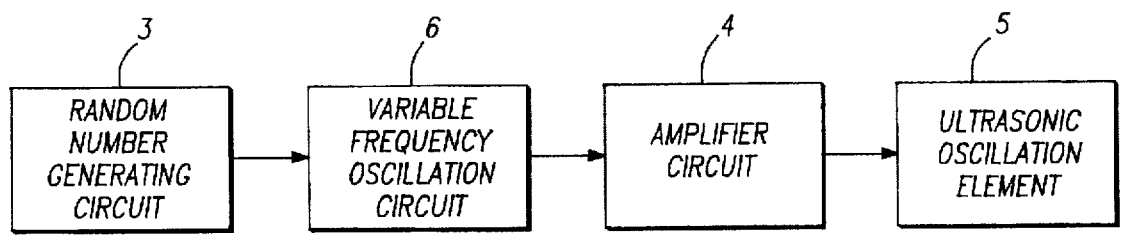
FIG. 3 is a block diagram showing a second embodiment of a remedial ultrasonic wave generating apparatus according to the present invention.

Features of the present invention will now be described in detail in preferred embodiments thereof with reference to the accompanying drawings.

FIG. 1 shows a first embodiment of a remedial ultra-sonic wave generating apparatus according to the present invention.

A plurality of oscillation circuits 1a through 1e oscillating at frequencies f1 through f5 in different ultrasonic frequency bands are provided. The output of each of the oscillation circuits 1a through 1e is supplied to a switching circuit 2 to which a random number generating circuit 3 is connected. According to a random number generated by the random number generating circuit 3, one of the outputs of the oscillation circuits 1a through 1e is selected to be supplied to an amplifier 4. The random number generating circuit 3 generates random numbers from "1" through "5". For example, when "1" is generated, the output at the frequency f1 from the oscillation circuit 1a is supplied to the amplifier 4; when "2" is generated the output at the frequency f2 from the oscillation circuit 1b is supplied to the amplifier 4; and so on.

The output of the switching circuit 2 is amplified by the amplifier 4 and is supplied to an ultrasonic oscillation element 5 attached to a remedial tool such as a catheter, utilizing an ultrasonic wave.

In the above-described ultrasonic wave generating apparatus, the outputs of the plurality of oscillation circuits 1a through 1e are selected according the random numbers. So, the frequency of the signal supplied to the amplifier 4 randomly changes in the range between f1 and f5 as shown in FIG. 2. Therefore, the ultrasonic oscillation element 5 generates ultrasonic waves having random frequencies. When the frequency of an ultrasonic wave randomly changes, the ultrasonic oscillation includes frequency components in a very wide band. As a result, the optimum frequency component is always available regardless of the varied conditions of the objects of the remedies, and sufficient effect can be obtained in remedies for the diseased parts.

A more detailed description will now be made on the reason for the improvement in the effect of a remedy obtained with randomly changing frequency of the ultrasonic wave. When the ultrasonic oscillation element oscillates at a single frequency, a substance contained in a liquid repeats a regular and linear movement. On the other hand, when an ultrasonic wave is applied at a plurality of frequencies, the substance makes a complicated movement which improves the effect of a remedy. Further, a substance in a liquid tends to move only at a particular frequency depending on its weight and size while the application of a plurality of frequencies allows substances in different sizes to be moved simultaneously.

From the characteristics of an ultrasonic oscillation element, it will be understood that the directivity of an ultrasonic wave at a particular frequency is fixed for the given size, weight, shape, etc. of the element. In other words, the ultrasonic wave travels only in a particular direction. Conversely, if the frequency of the ultrasonic wave is changed, the directivity changes with the frequency. Therefore, the application of a plurality of frequencies to an ultrasonic oscillation element will prevent directional deviation to provide an ultrasonic wave having improved directional uniformity.

FIG. 3 shows a second embodiment of a remedial ultrasonic wave generating apparatus according to the present invention. It is different from the first embodiment shown in FIG. 1 in that the plurality of oscillation circuits 1a through 1e oscillating at different frequencies and the switching circuit 2 are replaced by a variable frequency oscillation circuit 6 whose oscillation frequency is directly controlled by the random number generating circuit 3. Variable frequency oscillation circuit 6 may be a phase-locked loop circuit whose oscillation frequency is changed by controlling the frequency dividing ratio in accordance with the random number data from the random number generating circuit 3, a voltage controlled oscillation circuit whose oscillation frequency is changed according to an analog signal obtained by performing D/A-conversion on the random number data from the random number generating circuit 3, or the like.

Figure 4:
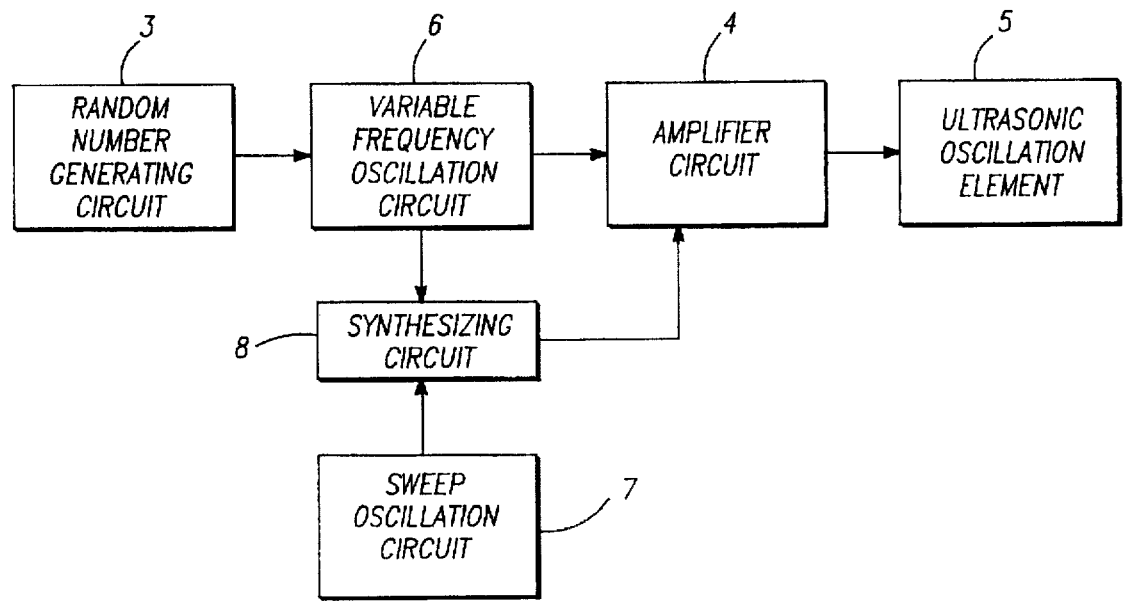
FIG. 4 is a block diagram showing a third embodiment of a remedial ultrasonic wave generating apparatus according to the present invention.
Figure 5:
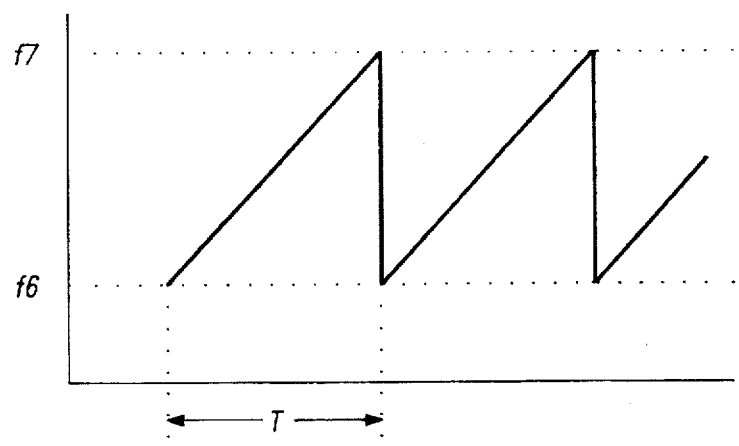
FIG. 5 is a graph showing changes in the output frequency of a sweep oscillation circuit.

FIG. 4 shows a third embodiment of a remedial ultrasonic wave generating apparatus according to the present invention. In this third embodiment, in addition to the configuration of the second embodiment shown in FIG. 3, there is provided a sweep oscillation circuit 7 whose oscillation frequency continuously changes in the form of teeth in the range between f6 and f7 in a cycle T as shown in FIG. 5. The sweep output of the sweep oscillation circuit 7 is synthesized with the random output from the above-mentioned variable frequency oscillation circuit 6 at a synthesizing circuit 8 and the product is supplied to the amplifier circuit 4. According to the third embodiment shown in FIG. 4, since the ultrasonic oscillation element 5 is applied with the signal having a continuously changing frequency from the sweep oscillation circuit 7 as well as the signal having a randomly changing frequency from the variable frequency oscillation circuit 6, the ultrasonic oscillation element 5 oscillates in a very complicated manner, thereby further improving the effect of a medicine. In addition, since the ultrasonic oscillation element 5 is applied with the signal having a continuously changing frequency, the ultrasonic oscillation element is driven at all the frequencies within the sweep frequency range without omission. As a result, the optimum frequency component is always available regardless of the varied conditions around the objects of remedies, and sufficient effect can be achieved on diseased parts.

In the above description, the presence of a wide range of frequency components in the output of the ultrasonic oscillation element 5 has been described as the reason that a remedy can be administered to a diseased part with sufficient effect regardless of the varied conditions at the site. This may lead one to assume that it is not essential to randomly change the frequency, and the frequency may be changed in an orderly fashion within a desired frequency range. However, changing the frequency in a particular order will not provide sufficient effect as described below.

In order to confirm the effect obtained by randomly changing the frequency of the ultrasonic waves, a cell lysis effect obtained by operating the ultrasonic oscillation element at random frequencies within a certain frequency band was compared to that obtained by operating the element by means of a continuously changing repetitive sweeping wave using frequencies in the same band. The method for the experiment was as follows.

White blood cells were separated from the blood of a rabbit, and ultrasonic waves were applied to the white blood cells for a predetermined period of time. The number of live white blood cells before application was compared to that after application. The conditions for the application of the ultrasonic waves were divided into groups A and B as shown below.

Group A (Example for Comparison): frequencies of 800 kHz, 1000 kHz, 1100 kHz and 1200 kHz were repeated in order for 0.2 sec each.

Group B: the same frequencies as in the group A were generated for the same period of time but in arbitrary combinations and order, i.e., they were randomly repeated.

The experiment was carried out using the same application time and ultrasonic output (approximately 0.5 W/cm$^2$).

The results are shown in FIG. 6. The broken line indicates the group A and the solid line indicates the group B. Time (sec.) is shown along the vertical axis and the survival rate of the cells (%) is shown along the axis of the abscissa. As shown in FIG. 6, random combinations (group B) exhibited a more significant effect in killing the white blood cells. After the total ultrasonic application time of 60 sec., the group A displayed a lysis of 20% of the cells while the group B displayed a lysis of 51%. This significant difference increased in proportion to the application time.

As described above, the cell breakage rate obtained using randomly changing frequencies was higher than that obtained by the frequencies changed in order, and it seems that there was an increase in energy efficiency. While the reasons for this are not clear, it is assumed that changing a frequency in order results in absorbance of the change in the frequency by the oscillation mode of a substance at the previous frequency, and is not likely to cause a change in the oscillation mode of the substance. Changing a frequency at random eliminates the influence of the oscillation mode of the substance at the previous frequency because the oscillation mode at each frequency is completely different from those at other frequencies.

As described above, according to the present invention, an ultrasonic oscillation element is driven at a random frequency. This provides the ultrasonic oscillation element with a varied oscillation mode and thereby improves the efficiency of dispensation of a medicine. The improvement in the efficiency of dispensation results in a reduction in ultrasonic application time. As a result, the amount of the energy required for ultrasonic oscillation can be reduced. The improvement in the efficiency of dispensation also allows the strength of the ultrasonic wave to be reduced, thereby eliminating problems for the patient. Further, an ultrasonic oscillation element can be used without the need to consider the directivity and frequency characteristics of the ultrasonic oscillation element itself. In addition, the optimum effect of a remedy can be achieved through a process which remains unchanged irrespective of the density, stiffness or the like of the tissues to be treated.

While the present invention has been shown and described with reference to the foregoing operational principles and preferred embodiments, it will be apparent to those skilled in the art that other changes in form and detail may be made therein without departing from the spirit and scope of the invention as defined in the appended claims.

What is claimed is:

1. A remedial ultrasonic wave generating apparatus, comprising:
    an ultrasonic wave signal generating means for generating an ultrasonic wave signal having a frequency that randomly changes, wherein said ultrasonic wave signal generating means comprises a plurality of oscillation circuits generating a plurality of outputs at different frequencies for improving dispensation and effect of a medicine to a patient, and a selection means for randomly selecting one of said plurality of outputs of said plurality of oscillation circuits; and
    a remedial ultrasonic oscillation element coupled to said ultrasonic wave signal generating means.

2. A remedial ultrasonic wave generating apparatus, comprising:
    an ultrasonic wave signal generating means for generating an ultrasonic wave signal having a frequency that randomly changes, wherein said ultrasonic wave signal generating means comprises a random number generating circuit and a variable frequency oscillation circuit having an oscillation frequency that is controlled by an output of said random number generating circuit for improving dispensation and effect of a medicine to a patient; and
    a remedial ultrasonic oscillation element coupled to said ultrasonic wave signal generating means.

3. A remedial ultrasonic wave generating apparatus for supplying an ultrasonic wave signal to a remedial ultrasonic oscillation element, comprising:
    an ultrasonic wave signal generating means for generating an ultrasonic wave signal having a frequency that randomly changes, wherein the ultrasonic wave signal generating means includes a plurality of oscillation circuits oscillating at different frequencies and producing a plurality of outputs, and a selection means for randomly selecting an output from the plurality of outputs of the plurality of oscillation circuits; and
    a sweep oscillation circuit having an oscillation frequency that continuously changes in a teeth pattern within a predetermined range and a synthesizing circuit for synthesizing an output of the sweep oscillation circuit and an output of the ultrasonic wave signal generating means.

4. A remedial ultrasonic wave generating apparatus for dispensing medicine in the vicinity of a diseased part, comprising:
    an ultrasonic wave signal generating means for generating an ultrasonic wave signal having a frequency that randomly changes for improving dispensation and effect of a medicine to a patient; and
    a remedial ultrasonic oscillation element coupled to the ultrasonic wave generating means.

5. A remedial ultrasonic wave generating apparatus according to claim 4, wherein said ultrasonic wave signal generating means comprises a plurality of oscillation circuits generating a plurality of outputs at different frequencies and a selection means for randomly selecting one of said plurality of outputs of said plurality of oscillation circuits.

6. A remedial ultrasonic wave generating apparatus accordingly to claim 4, wherein said ultrasonic wave signal generating means comprises a random number generating circuit and a variable frequency oscillation circuit having an oscillation frequency that is controlled by an output of said random number generating circuit.

7. A remedial ultrasonic wave generating apparatus configured for dispensing medicine in the vicinity of a diseased part, comprising:
    an ultrasonic wave signal generating means for generating an ultrasonic wave signal having a frequency that randomly changes; and
    a sweep oscillation circuit having an oscillation frequency that continuously changes in a teeth pattern within a predetermined range and a synthesizing circuit for synthesizing an output of the sweep oscillation circuit and an output of the ultrasonic wave signal generating means.

8. A medical ultrasound wave generating apparatus, comprising:
    a variable frequency oscillation circuit configured to produce an ultrasound energy output having a plurality of frequencies;
    a random number generating circuit coupled to the variable frequency oscillation circuit and configured to select a selected ultrasound energy output frequency from the variable frequency oscillation circuit; and
    an ultrasound energy applicator coupled to the random number generating circuit and configured to direct the ultrasound energy output corresponding to the selected ultrasound energy output frequency to a diseased site of a patient.

9. The apparatus of claim 8, wherein the interface is a part of a patient's body.

10. The apparatus of claim 8, wherein the ultrasound energy applicator is positioned at an interior of a patient's body.

11. The apparatus of claim 10, wherein the variable frequency oscillation circuit is a phase locked loop circuit.

12. A medical ultrasound wave generating apparatus, comprising: a plurality of oscillation circuits configured to produce a plurality of ultrasound energy outputs with a plurality of frequencies;

a switching circuit coupled to the plurality of oscillation circuits and configured to randomly select a selected ultrasound energy output from the plurality of ultrasound energy outputs;

an amplifier coupled to the switching and configured to receive and amplify the selected ultrasound energy output to form an amplified ultrasound energy output; and an ultrasound energy applicator coupled to the amplifier and configured to direct the amplified ultrasound energy output to a diseased site of a patient.

13. The apparatus of claim 12, wherein the interface is a part of a patient's body.

14. The apparatus of claim 12, wherein the ultrasound energy applicator is positioned at an interior of a patient's body.

15. The apparatus of claim 14, wherein the variable frequency oscillation circuit is a phase locked loop circuit.

* * * * *

UNITED STATES PATENT AND TRADEMARK OFFICE
CERTIFICATE OF CORRECTION

PATENT NO. : 5,720,710
DATED : February 24, 1998
INVENTOR(S) : Katsuro Tachibana and Shunro Tachibana It is certified that error appears in the above-identified patent and that said Letters Patent is hereby corrected as shown below:

<u>Title page,</u>
Item [73], Assignee, delete "Ekos Corporation, Bothell, WA (US)"

Signed and Sealed this

First Day of June, 2004

JON W. DUDAS
*Acting Director of the United States Patent and Trademark Office*